United States Patent [19]

Vitulli, Jr.

[11] Patent Number: 4,839,592
[45] Date of Patent: Jun. 13, 1989

[54] OPERATOR INPUT RESPONSIVE SYSTEM AND METHOD FOR SELECTIVELY IDENTIFYING VERIFIED OBJECT FLAWS

[75] Inventor: Joseph L. Vitulli, Jr., New Rochelle, N.Y.

[73] Assignee: Magnetic Analysis Corporation, Mount Vernon, N.Y.

[21] Appl. No.: 118,059

[22] Filed: Nov. 9, 1987

[51] Int. Cl.[4] ............... G01N 27/72; G01N 27/82; G01R 33/12
[52] U.S. Cl. .................... 324/227; 324/238
[58] Field of Search ............ 324/225, 226, 227, 238, 324/239, 240, 241, 242, 243

[56] References Cited

U.S. PATENT DOCUMENTS 3,673,493  6/1972  Hoffman et al. ............... 324/226
4,472,681  9/1984  Toth .................................. 324/226

Primary Examiner—Reinhard J. Eisenzopf
Assistant Examiner—Walter E. Snow
Attorney, Agent, or Firm—Robin, Blecker & Daley

[57] ABSTRACT

A system for verified detection of flaws in an object, comprises a synchronizing sensor for generating an output signal once per mutual rotational revolution as between itself and the object, a flaw sensor for generating output signals responsive to detection of flaws in the object and extraneous influences, a switch unit responsive to operator input for providing output signals respectively indicative of a preselected number of flaws for such flaw verification and of a preselected number of object revolutions for such flaw verification, and a processor responsible to the output signals of the sync sensor, the flaw sensor and the switch unit for providing verified flaw output indication.

10 Claims, 6 Drawing Sheets

OPERATOR INPUT RESPONSIVE SYSTEM AND METHOD FOR SELECTIVELY IDENTIFYING VERIFIED OBJECT FLAWS

FIELD OF THE INVENTION

This invention relates generally to nondestructive object examination and pertains more particularly to enhanced detection of flaws in object examination by the use of magnetic fields.

BACKGROUND OF THE INVENTION

Presently commercially known equipment for examination of objects for detection of flaws by the use of magnetic fields involves the disposition of the object in a magnetic field and effecting mutual rotational movement as between the object and flaw sensors. The sensors sense magnetic fields and generate output signals responsively to the sensing of changes in the ambient magnetic field occasioned by flaws in the object. One type of such equipment, embodying the so-called flux leakage method, is seen in U.S. Pat. No. 3,854,085, commonly-assigned herewith. Other types of such equipment, of eddy-current and EMAT (electromagnetic acoustic transducer) variety, are to be seen in U.S. Pat. No. 4,449,408, also commonly-assigned herewith. Incorporating reference is made hereby to such commonly-assigned patents.

In commercial practice heretofore, involving equipment of such assignee, Magnetic Analysis Corporation, and others involved in magnetic field object flaw examination, it has been customary to rely upon flaw intelligence gathered, per individual relative revolution of object and sensor, to reach a determination of the existence of an object flaw. This practice is problematic, especially in high noise environments, in that magnetic and electrical noise can give rise to faulty identifications of flaws not actually present in the object.

SUMMARY OF THE INVENTION

The present invention has as its primary object the provision of improved methods and systems for enhanced object flaw determination in magnetic field object examination.

A more particular object of the invention is to provide improved magnetic field object examination systems and methods wherein relative rotation takes place as between objects under examination and associated magnetic field sensor means.

In attaining the foregoing and other objects and features, the invention provides a system for verified detection of flaws in an object wherein the system is responsive to operator/user input as to selective standards of numbers of flaws and number of object/sensor revolutions to qualify a flaw sensor output as indicative of an actual flaw in the object only on compliance with such standards. To this end, the invention provides synchronization means for generating an output signal once per mutual rotational revolution as between such means and an object, flaw sensor means for generating output signals responsive to detection of flaws in the object and extraneous influences, switch means responsive to operator input for providing output signals respectively indicative of operator flaw number selection for verification and number of revolutions for such flaw verification, and processor means responsive to such output signals of the synchronization sensor means, the flaw sensor means and the switch means for providing verified flaw output indication.

The foregoing and other objects and features of the invention will be further understood from the following detailed description of preferred embodiments and practices and from the drawings wherein like reference numerals identify like parts throughout.

DESCRIPTION OF PREFERRED EMBODIMENTS AND PRACTICES

Figure 1:
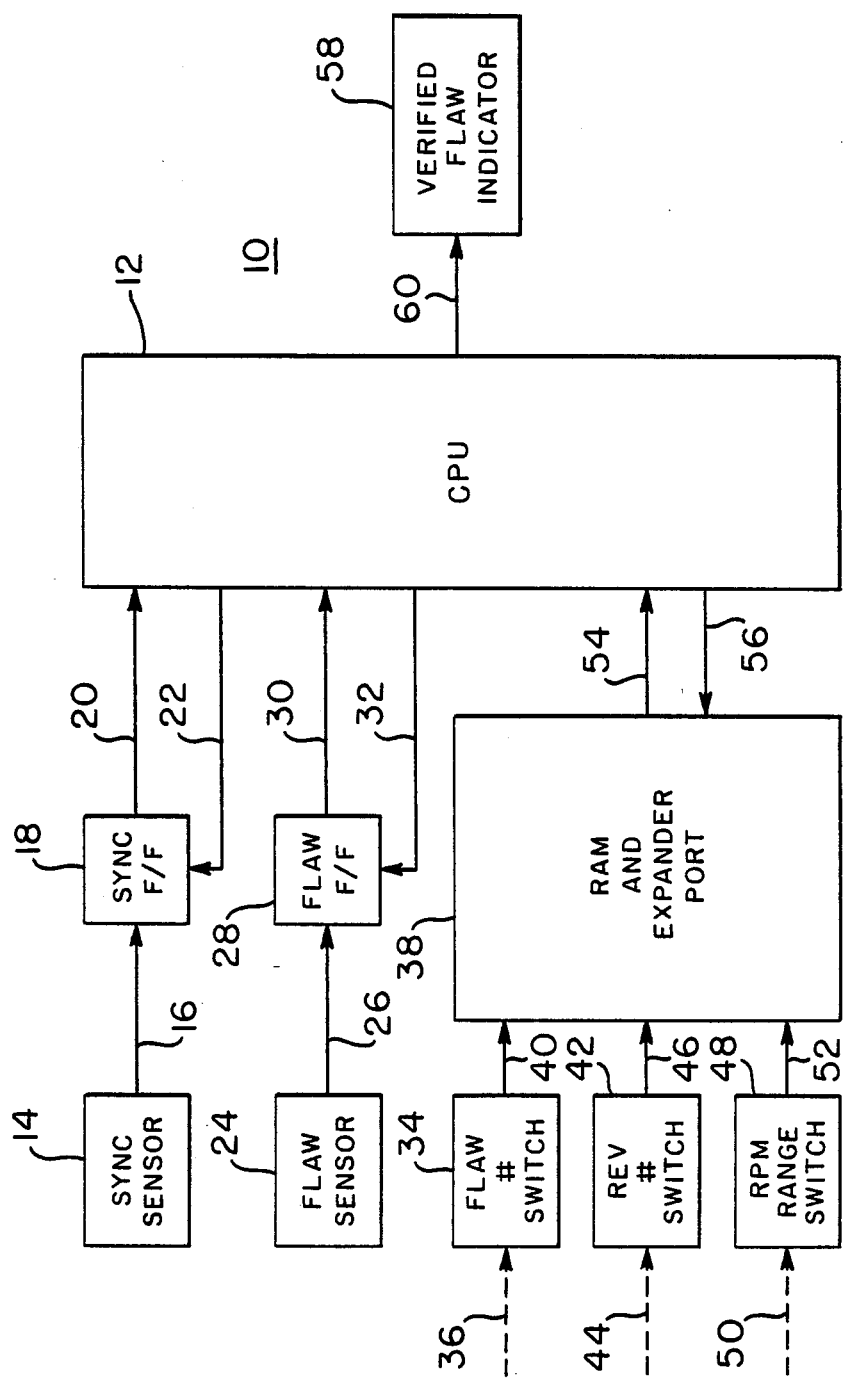
FIG. 1 is a block diagram of a system in accordance with the invention.

Referring to FIG. 1, system 10 of the invention includes a central processing unit 12 (CPU), which may be a microprocessor chip suitably programmed to implement the operations described below in connection with the flow charts of FIGS. 2 through 6.

Sync sensor 14 synchronizes operation of system 10 with the revolutional cycle of movement of an object under examination, such as a metal pipe (not shown). At the commencement of each revolution of the object, sensor 14 applies an output of signal indicative thereof to line 16 which sets Sync F/F 18. The state of Sync F/F 18 is furnished to CPU 12 over line 20 and the CPU resets this flip-flop over line 22.

Flaw sensor 24 is supported in operative relationship to the object to detect flaws therein and provides an output signal indicative of detected object flaws on line 26. Due to noise or other extraneous factors, sensor 24 will also provide output signals on line 26 although a flaw is not the cause thereof, as above discussed. Each such line 26 signal sets flaw F/F 28. The state of flaw F/F 28 is furnished to CPU 12 over line 30 and the CPU resets this flip-flop over line 32.

Flaw # switch 34 is settable by operator input 36 to indicate to system 10 the number of times a flaw is to be detected during a succession of object revolutions in order to qualify as a verified flaw. The output of this switch is parallel binary and is furnished to RAM and expander port 38 by lines 40, which will be selectively HI or LO in correspondence to input 36.

Rev # switch 42 is settable by operator input 44 to indicate to system 10 the number of object revolutions to be implemented in the course of reaching verified flaw qualification. The output of this switch, again parallel binary, is furnished to unit 38 over lines 46.

RPM range switch 48 is settable by operator input 50 to indicate to system 10 the range of revolutions per minute at which the object will be rotated. The parallel output of this switch is furnished to unit 38 over lines 52.

CPU 12 is informed of operator selections over lines 54 upon CPU inquiry over lines 56. CPU 12, upon decisional activity respecting its various inputs, selectively energizes verified flaw indicator 58 over line 60, responsively to signals on lines 20 and 30.

Switches 34, 42 and 48 allowed extensive user versatility in operating system 10. Through switch 48, the user may select rpm range selectively for different applications. Through switches 34 and 42, the user may set permutations for verified flaw qualification to his own specifications. Thus, a first user may require the reccurrence of flaw detection in each of five successive object revolutions. A second user may have satisfaction for flaw detection in any two of three successive object revolutions. In the former case, the user would set switch 34 to five and switch 42 to five. In the latter case, the user would set switch 34 to two and switch 42 to three.

The program implemented in CPU 12 will now be discussed with initial reference to FIG. 2. START is effected by user operation of a start switch (not shown), after setting of switches 34, 42 and 48 of FIG. 1. Step 64 (INITIALIZE HARDWARE AND REGISTERS), step 66 (CLEAR DATA MEMORY) and set 68 (READ PROGRAMMABLE INPUTS) follow, to effect customary CPU start conditions and the reading of inputs from switches 34, 42 and 48.

In step 70 (? RUN VERIFY PROGRAM), the operator may select, or not select, the present flaw verification system. If not selected (N, no), progress is to customary previously known practice. If selected (Y, yes), progress is to step 72 (PREPARE INPUT F/FS), wherein sync F/F 18 and Flaw F/F 28 of FIG. 1 are cleared.

In step 74 (? SYNC PRESENT), CPU 12 looks to line 20 of FIG. 1 to detect the sync signal. While not shown, CPU 12 recycles at step 74 until occurrence of the initial sync signal detection, step 74 Y output, whereupon progress is over flow line 75 to step 76 (RESET SYNC INPUT F/F) of FIG. 3 wherein sync F/F 18 of FIG. 1 is reset, then to step 78, wherein CPU 12 sets its revolution counter to one, then to step 80 (CLEAR MEMORY LOCATIONS), wherein CPU 12 reserves flaw storage memory, and then to step 82 (SET UP TIMER REGISTER), wherein the CPU timer register is caused to start its run. Such run is to time a prescribed subdivision of a revolution, for example, a twelve-degree interval thereof, thirty such intervals defining a full revolution and being "positions" therein, as further discussed below.

Figure 2:
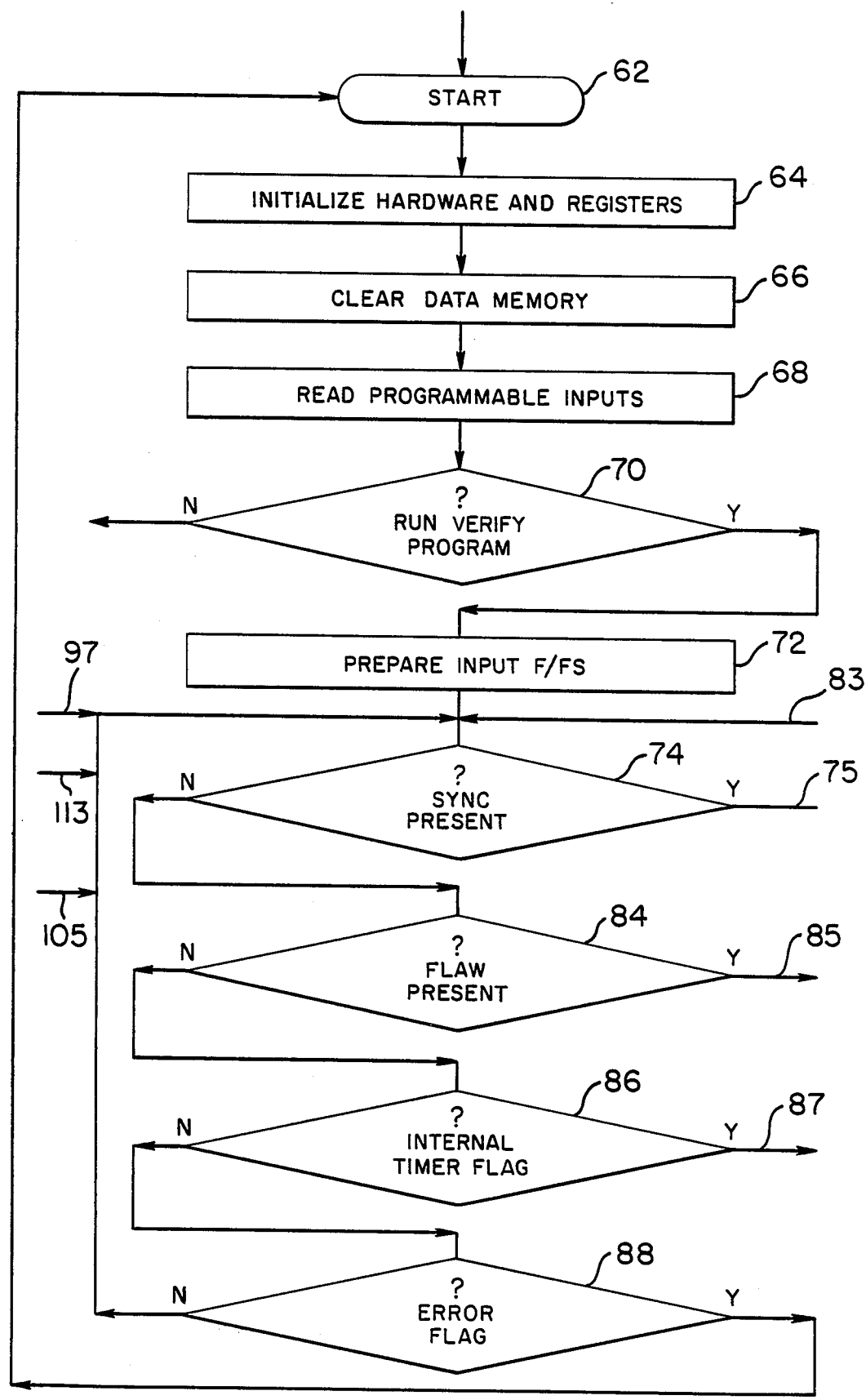
FIG. 2 through FIG. 6 are flow charts indicative of operational steps implemented in the FIG. 1 system.
Figure 3:
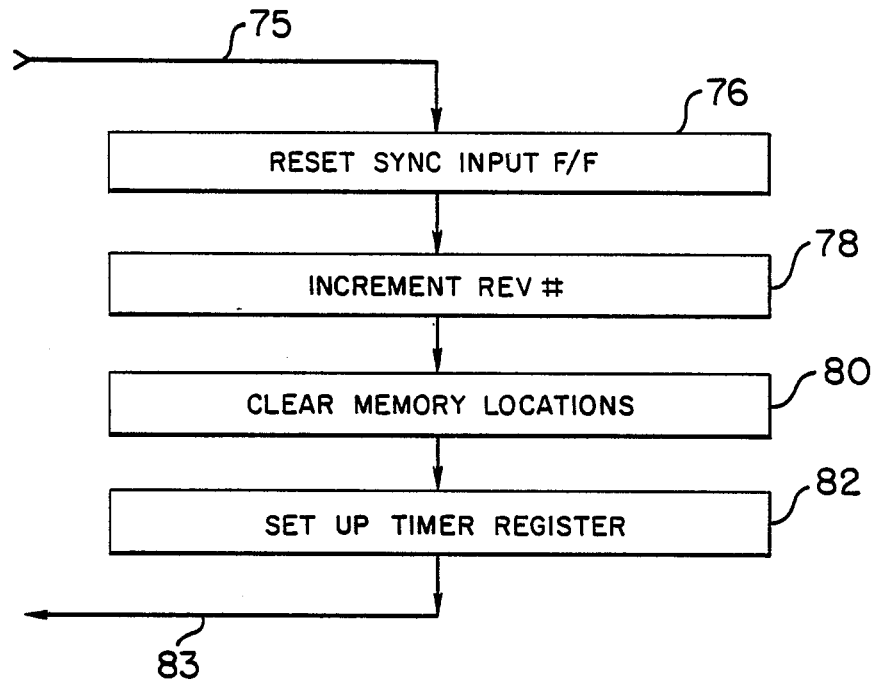
Figure 4:
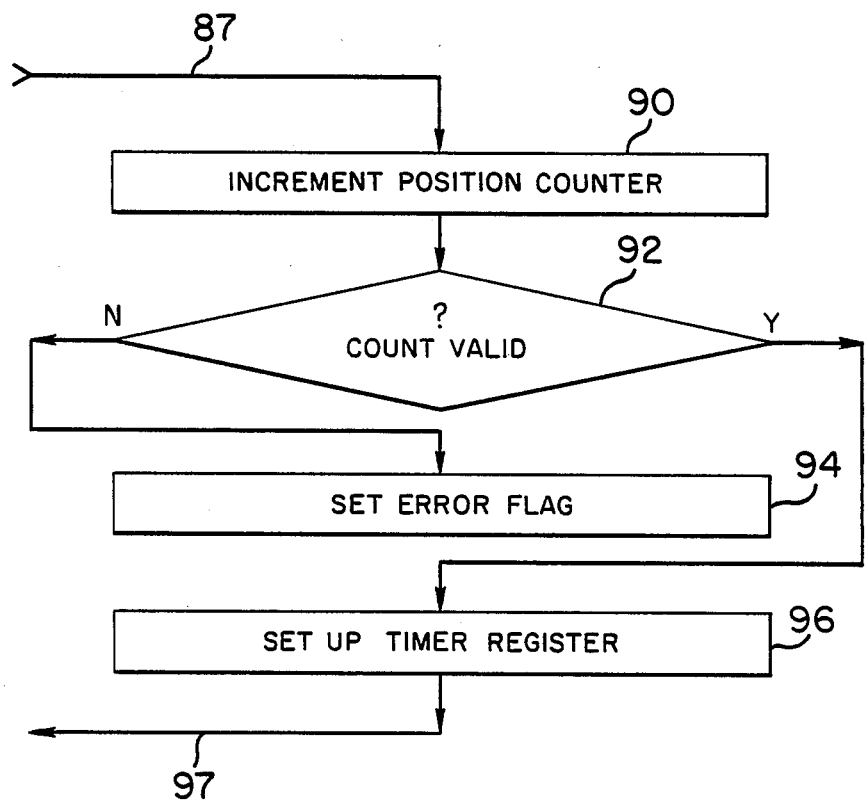
Figure 5:
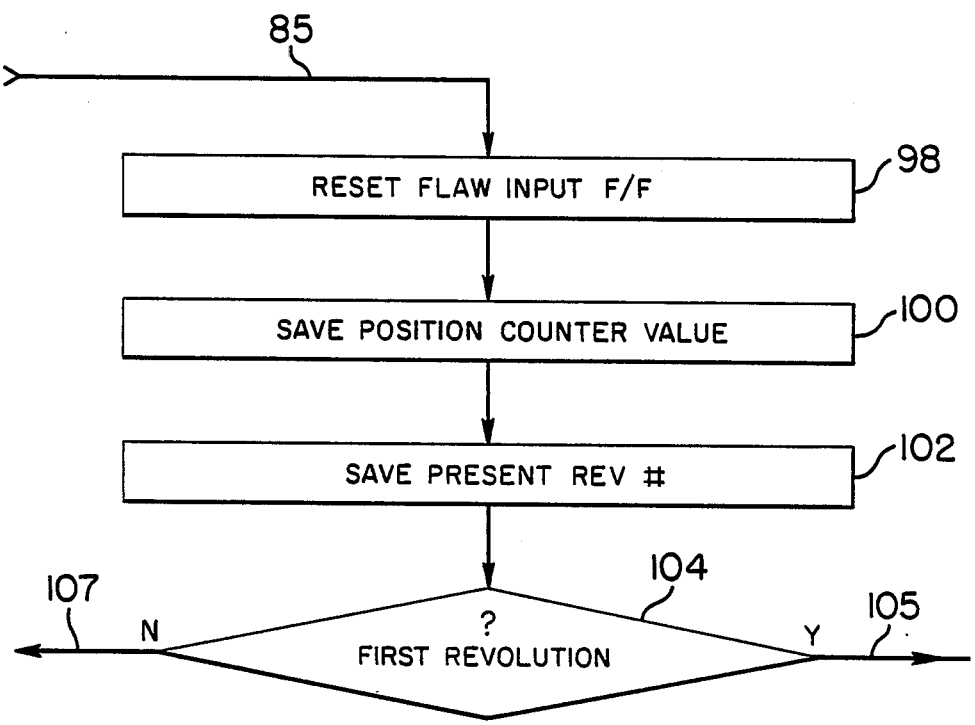
Figure 6:
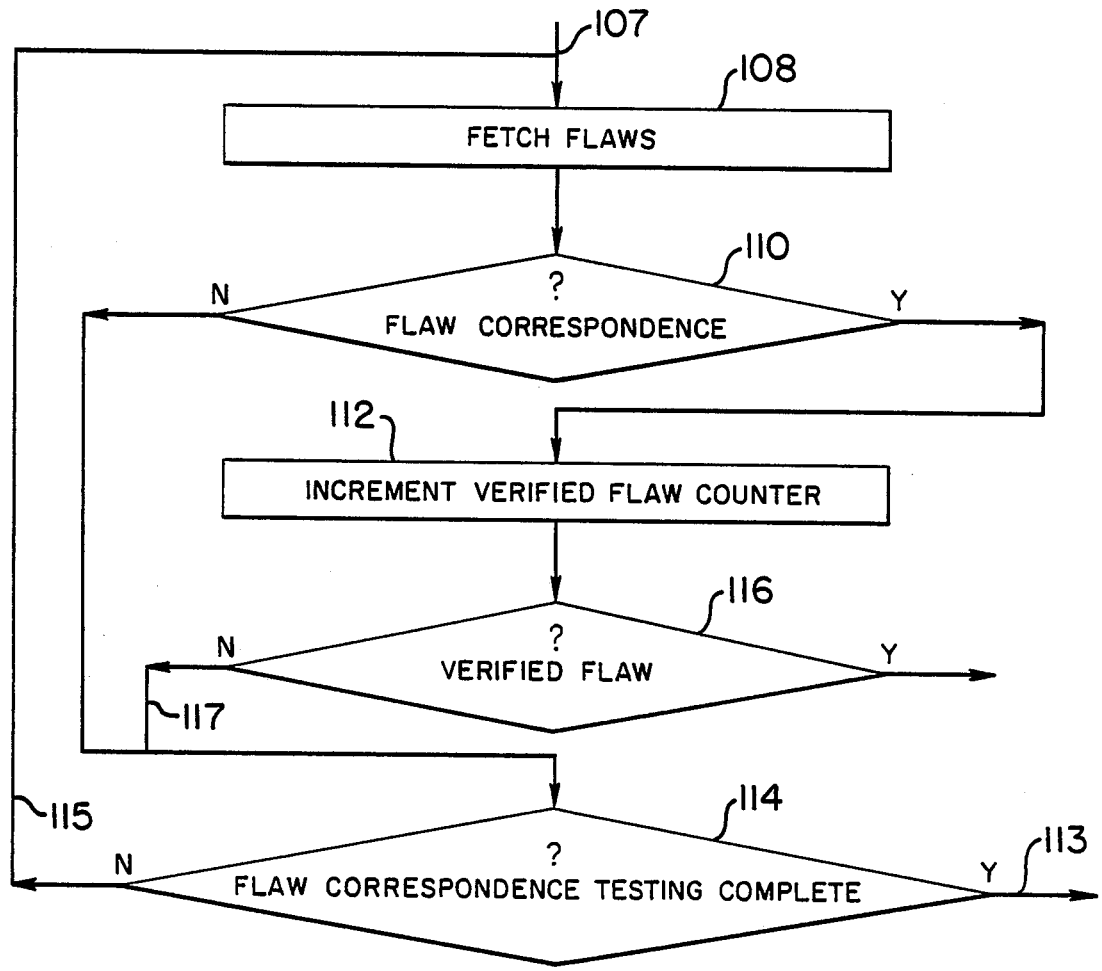

Following practice of the FIG. 3 steps, CPU 12 returns over flow line 83 to step 74 of FIG. 2. Since sync F/F 18 was reset in step 76, the step 74 inquiry is answered in the negative and pregress is to step 84 (? FLAW PRESENT), wherein CPU 12 looks to its line 30 (FIG. 1) input for state change of flaw F/F 28. Assuming the step 84 inquiry to be answered in the negative, advance is to step 86 (? INTERNAL TIMER FLAG). In this step, CPU 12 inquires as to whether the time period set up in step 82 has expired. Assuming the time period not to have expired, progress is to step 88 (? ERROR FLAG), where inquiry is made as to whether there is and error condition within the CPU. Assuming negative response to this step 88 inquiry, advance is to step 74. If the response is affirmative, advance is to START step 62.

To this juncture, conditions existing are that the initial sync has been detected, that a flaw has not been detected, that the CPU timer register has not reached its end, and that no error condition has been confronted.

Assuming now, in practice of step 74 that the next sync is not detected, as would be the case since the CPU timer register has not timed out, discussion further assumes that a flaw is not yet detected and that the CPU timer register times out. One thus has negatives from steps 74 and 84 and a positive from step 86. Progress is accordingly over flow line 87 to FIG. 4 and step 90 (INCREMENT POSITION COUNTER), wherein CPU 12 sets its position within revolution counter to the first (twelve degree) position. Advance is then to stop 92 (? COUNT VALID). In the twelve degree timer example at hand, positive counter valves are valid if between zero and thirty. If the count valid inquiry is negative, an error condition is noted in step 94 (SET ERROR FLAG).

Assuming valid position count, progress is to step 96 (SET UP TIMER REGISTER), wherein the CPU timer register recommences its count. Return is now over flow line 97 to step 74 of FIG. 2.

In the example at hand, first cycle position after initial sync has been reached without flaw detection. It is now assumed that an object flow detection occurs between cycle positions one and two. The inquiry of step 84 is accordingly answered in the affirmative and progress is over flow line 85 of FIG. 2 to step 98 (RESET FLAW INPUT F/F) of FIG. 5. In implementing this step, CPU 12 resets Flaw F/F 28 over line 32. The CPU position counter value (first) is saved in step 100 (SAVE POSITION COUNTER VALVE). The revolution at hand (first) is saved in step 102 (SAVE PRESENT REV. #). In step 104 (? FIRST REVOLUTION), inquiry is made as to whether the system is operating in its initial flaw detection and storage revolution. Under present circumstances, the answer is affirmative and progress is over line 105 to step 74. As will be seen, the system cycles in the described manner throughout the first revolution, at the end of which memory will include indications of detected flaws by cycle position of detection and flagged as first revolution potential flaws.

In the course of the second and later revolutions, as each new flaw sensor output gives rise to possible flaw indication, the above practice occurs, however, with the difference that the answer to the inquiry of step 104 is negative. This leads to line 107 entry to the comparison flowchart of FIG. 6 and to step 108 (FETCH FLAWS). Assuming the revolution to be the second revolution and the flaw detection cycle position to be the second cycle position as respects the newly detected flaw, the inquiry of step 110 (? FLAW CORRESPONDENCE) will be answered in the affirmative since there is a flaw in this cycle position in the prior (first revolution) and such answer causes practice of step 112 (INCREMENT VERIFIED FLAW COUNTER). The verified flaw counter is thus set at one, indicating that there has been one verification of a flaw at this cycle position. As will be appreciated, flaw verification count is performed separately per cycle position and, in the twelve degree cycle length example, thirty separate such counts will be arranged for.

Practice of the flaw correspondence step 110 is performed successively backward through all prior revolutions. Thus, the flaw verification counter is stepped cumulatively, as will be further explained by the example of FIG. 7 and discussion below.

If the inquiry above in step 110 is answered in the negative, meaning that there is no flaw correspondence, progress is to step 114 (? FLAW CORRESPONDENCE TESTING COMPLETE) as to whether all prior cycles have been examined for correspondence with the current flaw candidate. If the inquiry is answered in the negative, progress is over line 115 to step 108 for continuance of the correspondence testing. If the inquiry is affirmatively answered, progress is over line 113 to step 74 of FIG. 2.

Upon each incrementing of each cycle position verified flaw counter, the system is operative to make inquiry in step 116 (? VERIFIED FLAW) as to whether the count state meets the criteria for verified flaw output. CPU 12 of FIG. 1 makes this determination on the basis of the inputs from units 34 and 42, from the state of its revolution counter and the state of the verified flaw counter for the cycle position under present consideration. In the absence of determining that a verified flaw condition is at hand, progress is over line 117 to step 114. On the other hand, if there is a yes answer, CPU 12 activates verified flaw indicator 58 of FIG. 1.

Figure 7:
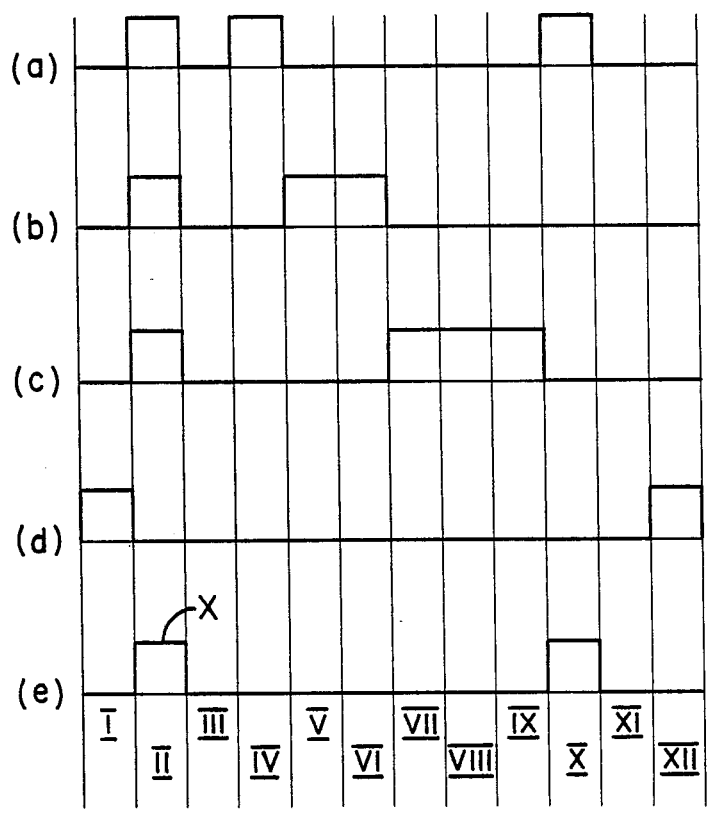
FIG. 7 depicts pulse patterns informative of system operation.

Turning To FIG. 7, parts (a) through (e) indicate the output signals of flaw F/F 30 of FIG. 1 for five successive revlolutions. The twelve cycle positions for the example under discussion are indicated as I through XII. As will be seen, the state changes indicative of potential flaws exhibit various cycle position repetitions which, in the absence of the subject flaw verification practice could all qualify as object flaws.

In position II, repetitive signals are seen in parts (a), (b), (c) and (e). In position X, repetitive signals are seen in parts (a) and (e).

If the verification criteria selected by an operator involve three repetitions over five revolutions, the signals in position II only would qualify as a verified flaw. If the verification criteria selected involve five repetitions over five revolutions, no flaw verification occurs. If the qualification standard were two repetitions in five revolutions, positions II and X would qualify as verified flaws.

As noted above, practice in step 116 is performed cumulatively backwardly. For example, in the four repetition, five revolution criteria, for the FIG. 7 flaw sensing pattern, when the system enters the fifth revolution, and is at the second cycle position, the flaw candidate marked X is confronted. The cycle position flaw counter is cleared and corresponding flaws in the first, second, third and fourth revolutions which are confronted in the comparison in step 110 successively step the counter to three, indicating the fourth repetition and calling for verified flaw output indication.

The FIG. 7 example explains the most simple occurrence of the flaw candidates, where each flaw candidate is shown as occurring exactly at the start of each cycle position, I through XII. In reality, the flaw candidate may occur at any point in time within a cycle position. CPU 12 of FIG. 1 will make the required determination of a verified flaw condition, thus allowing for variation within the cycle. Further, while twelve, thirty degree divisions are shown in the example, one can of course choose any desired division, such as, thirty, twelve degree divisions.

Various changes in practice and modifications to system arrangement and implementation may be introduced without departing from the invention. Accordingly, it is to be understood that the particularly described and discussed preferred embodiment is intended in an illustrative and not in a limiting sense. The true spirit and scope of the invention is set forth in the following claims.

What is claimed is:

1. A system for verified detection of flaws in an object, comprising:
   (a) sync sensor means for generating an output signal once per mutual rotational revolution as between said sync sensor means and said object;
   (b) flaw sensor means for generating output signals responsive to detection of flaws in said object and extraneous influences;
   (c) switch means responsive to operator input and separately settable for providing output signals respectively indicative of a first preselectable number of flaws for such flaw verification and a second preselectable number of object revolutions for such flaw verification; and
   (d) processor means responsive to said output signals of said sync sensor means, said flaw sensor means and said switch means for providing verified flow output indication, said output indication being selectively indicative of flaw verification for number of said object revolutions diverse from said preselected number of object revolutions when said switch means is set with respectively different first and second numbers.

2. The invention claimed in claim 1 wherein said switch means is further responsive to operator input for providing an output signal indicative of a preselected rate of such rotational revolution as between said sync sensor means and said object.

3. The invention claimed in claim 1 wherein said sync sensor means comprises a sync sensor for generating a signal one per such mutual rotational revolution as between same and said object and latchable sync means responsive to such sensor means generated signal for providing said sync sensor means output signal, said processor means including facility for selectively resetting said latchable sync means.

4. The invention claimed in claim 1 wherein said flaw sensor means comprises a flaw sensor for generating signals responsive to detection of such flaws in said object and such extraneous influences and latchable flaw means for providing said flaw sensor means output signal, said processor means including facility for selectively resetting said latchable flaw means.

5. The invention claimed in claim 1 wherein said processor means is operable for storage of occurrences of said flaw sensor means output signal per each such rotational revolution as between said sync sensor means and said object.

6. The invention claimed in claim 5 wherein said processor means is further operable for mutual comparison of such stored signals.

7. The invention claimed in claim 5 wherein said processor means is further operable for comparison of stored signals of one such revolution with stored signals of another such revolution.

8. The invention claimed in claim 4 wherein said processor means is responsive to said sync sensor means output signal to identify, per each such revolution, successively spaces positions in such revolution and to store occurences of said flaw sensor means output signals in correlation with such positions.

9. The invention claimed in claim 8 wherein said processor means is further operative to generate said verified flaw output indication on the basis of positive comparison, on a positional basis, of stored flaw occurences from different such revolutions.

10. A method for use in determining the existence of flaws in an object through the use of a flow sensor generating output signals responsively to actual flaws in said object and extraneous influences not indicative of actual flaws in said object, said method including the steps of:
   (a) effecting mutual cyclical movement as between said flaw sensor and said object:
   (b) generating an output signal indicative of the start of each such cycle of said movement;

(c) defining a plurality of cycle positions successive to each such cycle start output signal for each such cycle;

(d) storing each flaw sensor cycle output signal with indication therewith of its cycle of occurrence and its cycle position occurrence; and (e) preselecting first and second numbers respectively indicative of the number of flaws to occur for flaw verification and the number of such cyclic movements to occur for flaw verification, such preselected numbers being selectable as mutually equal or diverse.

* * * * *